(12) United States Patent
Gesotti (10) Patent No.: US 6,704,603 B1
(45) Date of Patent: Mar. 9, 2004

(54) ADAPTIVE STIMULATOR FOR RELIEF OF SYMPTOMS OF NEUROLOGICAL DISORDERS

(75) Inventor: Phil E. Gesotti, Manassas, VA (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

(21) Appl. No.: 09/659,351

(22) Filed: Sep. 12, 2000

Related U.S. Application Data (60) Provisional application No. 60/204,404, filed on May 16, 2000.

(51) Int. Cl.[7] .................................................. A61N 1/08
(52) U.S. Cl. ........................................................ 607/62
(58) Field of Search .............................. 607/45, 46, 62, 607/48, 49, 58; 128/905; 600/595, 546

(56) References Cited

U.S. PATENT DOCUMENTS

| | | |
|---|---|---|
| 4,165,750 A | 8/1979 | Aleev et al. |
| 4,340,063 A | 7/1982 | Maurer |
| 4,580,339 A | 4/1986 | Ioffe |
| 4,669,480 A | 6/1987 | Hoffman |
| 4,697,808 A | 10/1987 | Larson et al. |
| 4,754,759 A | 7/1988 | Allocca |
| 4,759,368 A | 7/1988 | Spanton et al. |
| 4,769,881 A | 9/1988 | Pedigo et al. |
| 4,917,092 A | 4/1990 | Todd et al. |
| 4,922,908 A | 5/1990 | Morawetz et al. |
| 4,989,605 A | 2/1991 | Rossen |
| 5,038,797 A | 8/1991 | Batters |
| 5,121,747 A | 6/1992 | Andrews |
| 5,184,617 A | 2/1993 | Harris et al. |
| 5,330,515 A | 7/1994 | Rutecki et al. |
| 5,330,527 A | 7/1994 | Montecalvo et al. |
| 5,350,414 A | 9/1994 | Kolen |
| 5,562,707 A * | 10/1996 | Prochazka et al. ............. 607/2 |
| 5,597,309 A | 1/1997 | Riess |
| 5,814,093 A | 9/1998 | Stein |
| 5,895,416 A | 4/1999 | Barreras, Sr. et al. |
| 5,961,542 A | 10/1999 | Agarwala |
| 5,964,789 A | 10/1999 | Karsdon |
| 6,016,449 A | 1/2000 | Fischell et al. |
| 6,044,303 A | 3/2000 | Agarwala et al. |
| 6,083,156 A | 7/2000 | Lisiecki |
| 6,094,598 A | 7/2000 | Elsberry et al. |
| 6,246,912 B1 | 6/2001 | Sluijter et al. |
| 6,356,784 B1 * | 3/2002 | Lozano et al. ................ 604/22 |

FOREIGN PATENT DOCUMENTS

| | | |
|---|---|---|
| EP | 0 911 061 A2 | 4/1999 |
| WO | WO 90/12293 | 10/1990 |
| WO | WO 97/39795 | 10/1997 |
| WO | WO 97/39796 | 10/1997 |

OTHER PUBLICATIONS

Choi et al. "Selectivity of Multiple–Contact Nerve Cuff Electrodes: A Simulation Analysis," *IEEE Transactions of Biomedical Engineering*, vol. 48, No. 2, pp. 165–172 (Feb., 2001).

Popovic et al. "Surface–Stimulation Technology for Grasping and Walking Neuroprostheses," *IEEE Engineering in Medicine and Biology* pp. 82–93 (Jan./Feb., 2001).

Riess et al. "Augmented Reality and Parkinson's Disease," (2 pgs.) http://ftp.hitl.washington.edu/publications/r–99–5/ (Jan. 22, 2002).

* cited by examiner

*Primary Examiner*—George R. Evanisko
(74) *Attorney, Agent, or Firm*—Fogg and Associates, LLC (57) ABSTRACT

An adaptive stimulator that aids in the relief of the symptoms of neurological disorders is provided. The adaptive stimulator is adapted to selectively provide stimulation in response to a control unit. The stimulator includes at least one stimulation electrode coupled to an output of the control unit. The at least one stimulation electrode is adapted to provide stimulation to an area of the body of a living subject. The adaptive stimulator includes at least one sensor coupled to the control unit and adapted to be disposed external to the body. The at least one sensor is adapted to respond to physical stimulus and provide input to the control unit.

23 Claims, 10 Drawing Sheets

Fig. 15 Stimulation Neckband (Rear View)

Fig. 14 Stimulation and Sensing Headband (Front View)

Fig. 16

Fig. 17

ADAPTIVE STIMULATOR FOR RELIEF OF SYMPTOMS OF NEUROLOGICAL DISORDERS

CROSS REFERENCE TO RELATED APPLICATIONS

This application is related to and claims the benefit of the filing date of provisional application Ser. No. 60/204,404 (the '404 Application), filed on May 16, 2000. The '404 Application is incorporated by reference.

TECHNICAL FIELD

The present invention relates generally to the field of electronics and, in particular, to the relief of Parkinson's disease symptoms using electrical stimulation.

BACKGROUND

Parkinson's disease is a neurodegenerative disorder that affects approximately one percent of the population over age 50 and up to two and a half percent of the population over age 70. The disease is currently of unknown origin, but appears to be the result a deficiency in dopamine (a neurotransmitter) due to the degeneration of an area of the brain known as the substantia nigra pars compacta.

Currently there is no diagnostic test for Parkinson's disease and diagnosis is based on the presence of characteristic symptoms and elimination of other potential causes through magnetic resonance imaging (MRI). At this time there is no cure for Parkinson's disease, only treatment to relieve the symptoms. The cardinal symptoms of Parkinson's disease are paucity of spontaneous movements, slowness of movement, rigidity of muscle tone, and the characteristic tremor at rest. In addition, there is often a mask-like facial expression and flexed posture. Treatment with medication to relieve the symptoms of Parkinson's disease is typically effective in the early stages of the disease's progression. However, the medication's effectiveness is highly variable from patient to patient. Medications also have undesirable side effects that get worse with increased dosage. As the disease progresses, it becomes more difficult to meter the medication to bring symptomatic relief while minimizing side effects. For example, some patients may be able to manage symptoms effectively with medication for 25 years. While other patients may experience intolerable side effects from increased dosage of medication within 5 years. The rate of disease progression is also highly variable.

When medication can no longer effectively manage symptoms, the patient has limited options. These include brain surgeries that lesion specific overactive areas in the brain and implanted electrodes in overactive brain areas that are controlled by a pacemaker-like device for stimulation. The stimulation appears to dampen the firing of overactive neurons providing similar symptomatic relief to the lesions. These surgical procedures are high-risk with the potential for causing hemorrhaging, blindness, or stroke.

Loss of sensing function is the major contributor to manifestation of symptoms associated with Parkinson's disease. The loss of sensing function or inability to process sensing information leads to problems with joint position sense (observation). This in turn leads to instability in the control loops of the Basil Ganglia, causing oscillation (tremor), out of phase control signals (rigidity), and the inability to initiate a relative motor plan (akinesia) and slowed movement execution (bradykinesia). The instability results in the presentation of symptoms where a patient is unaware of a bent arm, drooping head, stooped posture, slowed gait, or lack of arm swing. As a result there is a need in the art to provide relief to patients affected with Parkinson's disease.

For the reasons stated above, and for other reasons stated below which will become apparent to those skilled in the art upon reading and understanding the present specification, there is a need in the art for improvements in techniques to provide patients affected with Parkinson's disease relief from the symptoms.

SUMMARY

The above mentioned problems with treatment of the symptoms of Parkinson's disease and other problems are addressed by embodiments of the present invention and will be understood by reading and studying the following specification.

In one embodiment, an adaptive stimulator is provided. The stimulator includes a control unit and at least one stimulation electrode coupled to an output of the control unit. The at least one stimulation electrode is adapted to provide stimulation to an area of the body of a living subject. The adaptive stimulator includes at least one sensor coupled to the control unit and adapted to be disposed external to the human body. The sensor is adapted to respond to physical stimulus and provide input to the control unit. The adaptive stimulator is adapted to selectively provide stimulation in response to the control unit.

In another embodiment, a method of adaptive stimulation is provided. The method includes receiving one or more input signals. At least one of the input signals is based on physical stimulus. The method also includes monitoring the received input signals and selectively generating one or more stimulation signals when the one or more input signals meet defined criteria. The method further includes transmitting the one or more stimulation signals to an area of the body of a living subject. The one or more stimulation signals aid in the relief of symptoms of neurological disorders.

In another embodiment, a control unit adapted to aid in the relief of symptoms of Parkinson's disease is provided. The control unit includes an input that is adapted to couple to one or more sensors that are adapted to respond to physical stimulus. The control unit also includes a controller that is coupled to the input and a waveform generator coupled to the controller. The control unit further includes an output coupled to the controller and adapted to couple to one or more stimulation electrodes that are adapted to provide stimulation to an area on the human body. In addition, the control unit includes a stimulation voltage pulse generator coupled to the controller.

DETAILED DESCRIPTION

In the following detailed description, reference is made to the accompanying drawings that form a part hereof, and in which is shown by way of illustration specific illustrative embodiments in which the invention may be practiced. These embodiments are described in sufficient detail to enable those skilled in the art to practice the invention, and it is to be understood that other embodiments may be utilized and that logical, mechanical and electrical changes may be made without departing from the spirit and scope of the present invention. The following detailed description is, therefore, not to be taken in a limiting sense.

Figure 1:
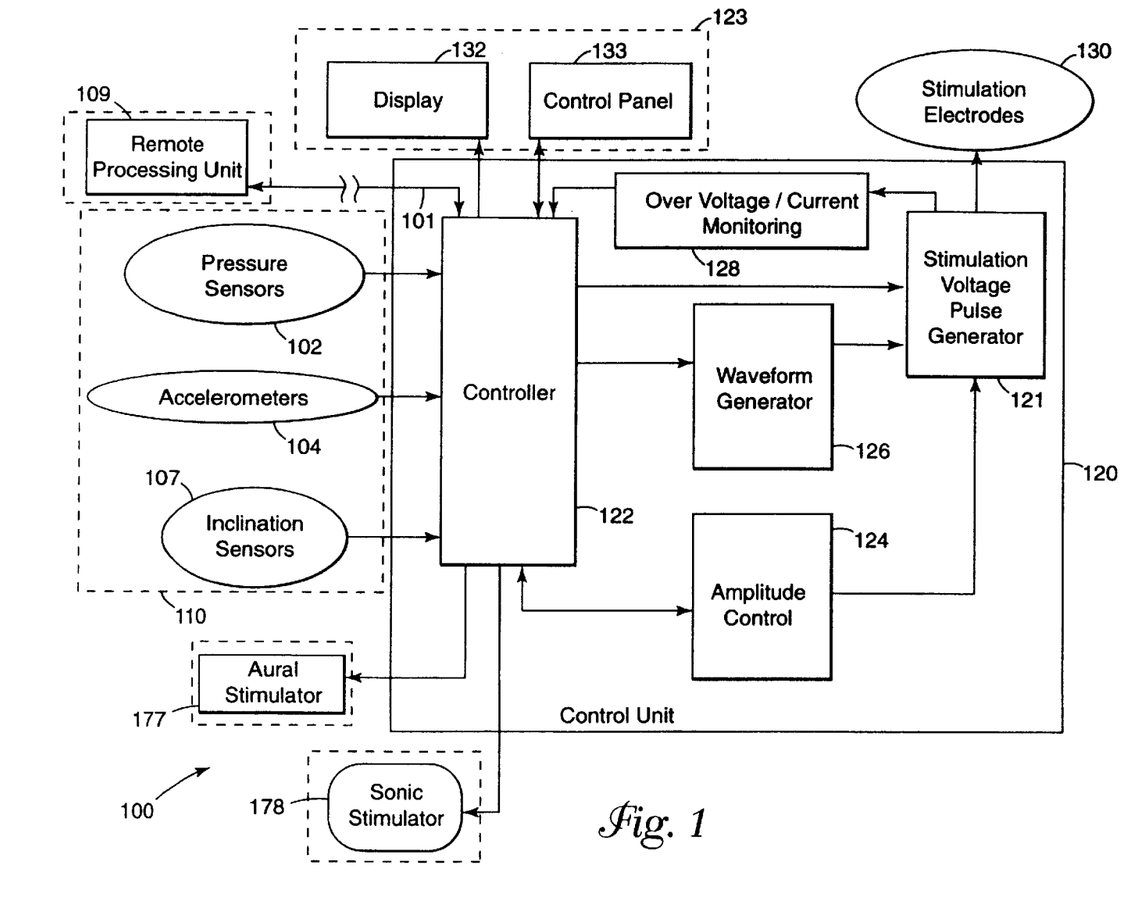
FIG. 1 is a block diagram of an embodiment of an adaptive stimulator constructed according to the teachings of the present invention.

FIG. 1 is a block diagram of one embodiment of an adaptive stimulator, shown generally at 100, constructed according to the teachings of the present invention. Adaptive stimulator 100 includes a control unit 120 coupled to at least one sensor 110. The at least one sensor 110 is responsive to physical stimulus such as pressure, acceleration, inclination or the like. In addition, adaptive stimulator 100 includes one or more stimulation electrodes 130 coupled to an output of control unit 120. Each stimulation electrode 130 or more than one electrodes 130 include a common return electrode. The common return electrode is in direct contact with the skin and provides the return path for each of the electrical stimulation electrodes attached to the body. It provides a large surface and as a result a lower impedance than each of the stimulation electrodes, this will aid in keeping the current at the contact location at a comfortable level for the patient. Each sensor 110 is strategically located to receive information based on human body functions such as tactility (pressure), movement (acceleration), placement (inclination) and the like. Each sensor 110 provides information to control unit 120. Control unit 120 receives the information and uses the information to determine when electrical stimulation is required at the location of each stimulation electrode 130. Control unit 120 selectively adjusts stimulation voltage, frequency, pulse width, waveform shape, amplitude, modulation type and the like of each electrical stimulation signal based on sensor information. Modulation type allows selection of one of a collection of dynamic waveform changes that vary amplitude, frequency or pulse width in some predetermined manner. In some applications, the body adapts to static waveforms decreasing sensitivity and this modulation feature prolongs stimulation effectiveness.

In one embodiment, adaptive stimulator 100 includes a display 132 coupled to control unit 120. In another embodiment, adaptive stimulator 100 includes a control panel 133 coupled to control unit 120. In an alternate embodiment, adaptive stimulator 100 includes an integrated display and control panel 123 coupled to control unit 120. Control panel 133 and integrated control panel 123 provide an operator interface for modification of operation of adaptive stimulator 100. In an embodiment, having a standalone control panel 133 or integrated control panel 123, control unit 120 selectively adjusts stimulation voltage, frequency, pulse width, waveform shape, amplitude, modulation type and the like based on sensor information and operator controls.

In one embodiment, control unit 120 includes a controller 122 that receives information from sensors 110. Controller 122 includes software that includes algorithms for processing the information from input signals and determines the response(s) required to produce simulation and stimulation. The controller 122 generates the basic timing for the stimulation waveforms and adjusts frequency, pulse width, waveform shape, and amplitude based on sensor information or sensor information and operator controls.

In one embodiment, control unit 120 includes a stimulation voltage pulse generator 121 coupled to an output of controller 122. Stimulation voltage pulse generator 121 produces individual stimulation signals for each stimulation electrode 130. In one embodiment, stimulation signals are phased, as non-overlapping pulses, to prevent unwanted cross coupling of currents between stimulation electrodes 130. Control unit 120 further includes a waveform generator 126 coupled between controller 122 and stimulation voltage pulse generator 121. Waveform generator 126 receives input from controller 122 and generates waveforms for input to stimulation voltage pulse generator 121. In addition, control unit 120 includes an over voltage/current monitoring circuit 128 coupled between stimulation voltage pulse generator 121 and controller 128. Monitoring circuit 128 monitors stimulation electrode voltage and current and provides information to controller 122 to prevent exposure of the patient to uncomfortable stimulation levels. In one embodiment, control unit 120 includes an amplitude control device 124 coupled between controller 122 and stimulation voltage pulse generator 121.

In one embodiment, adaptive stimulator 100 includes a telemetry link 101. Data is transmitted from control unit 120 to a remote processing unit 109 for further collection and processing of data obtained. In one embodiment, control unit 120 retains information about the operation of the adaptive stimulator 100 to include inputs to and outputs from control unit 120. In one embodiment, the information is used to track the progress of the disease and to monitor the operation of adaptive stimulator 100. In one embodiment, the information collected includes sensor and stimulator information. In another embodiment, the information further includes patient information and other data input to the control unit via control panel 133 and/or remote processing unit 109. In one embodiment, the information is stored in a database, a memory device or the like that is included in control unit 120. In one embodiment, the information is transmitted to remote processing unit 109 and stored by remote processing unit 109. In another embodiment, the information is wirelessly transmitted to remote processing unit 109. In one embodiment, the information is stored remotely by remote processing unit 109 for processing by any one of control unit 120, remote processing unit 109 or another device directly coupled to control unit 120 or coupled to control unit 120 via remote processing unit 109.

In one embodiment, adaptive stimulator 100 includes one or more aural stimulators 177. In one embodiment, the aural stimulator 177 includes a headphone and is driven by controller 122. In one embodiment, the headphones provide aural cues for drooping or tilted head and cadence for walking and repetitive activities.

In one embodiment, sensor 110 includes a pressure sensor located on an external region of the body. Control unit 120 interrogates the pressure sensor and receives pressure data. The control unit 120 determines if the pressure data meets a certain threshold or criteria. When the pressure data meets or exceeds the determined threshold, the control unit 120 generates stimulation signals and transmits the signals to stimulation electrodes 130. In one embodiment, the stimulation electrodes are located so as to provide a cue to the finger.

Figure 2:
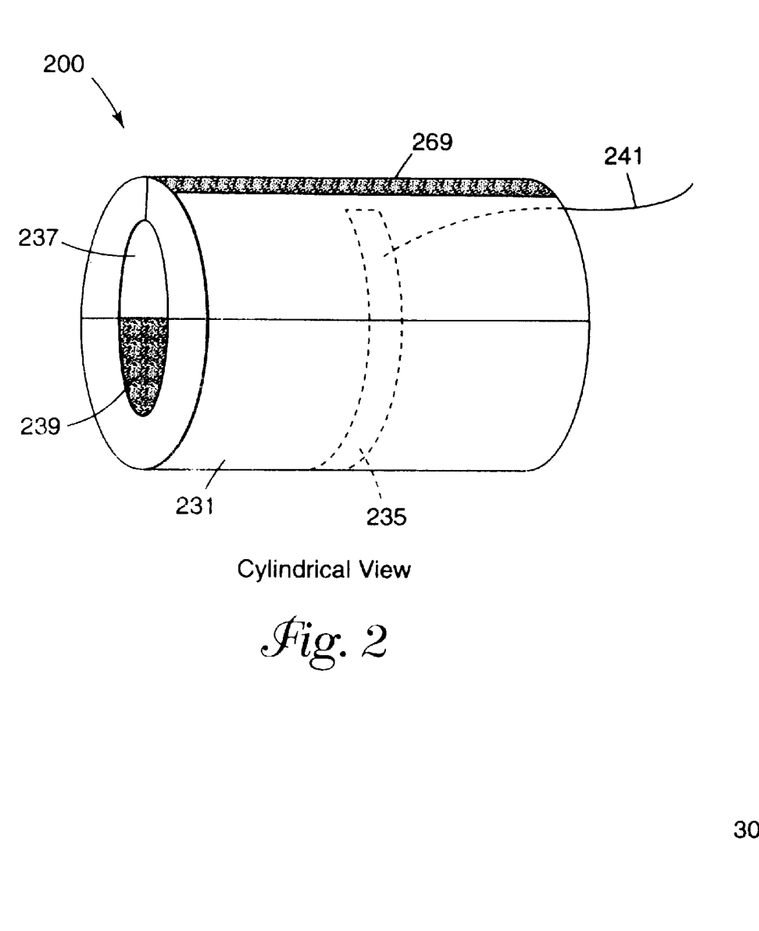
FIG. 2 is an illustration of a cylindrical view of one embodiment of a cylindrical stimulation electrode constructed according to the teachings of the present invention.

FIG. 2 is an illustration of a cylindrical view of one embodiment of a cylindrical stimulation electrode, shown generally at 200, constructed according to the teachings of the present invention. Stimulation electrode 200 includes a flexible conductor 235 that aids in fitting the electrode 200 around fingers, thumbs, wrist, ankle and other cylindrically shaped regions of the body. Conductor 235 is coupled to an electrical lead 241 that is coupled to and receives electrical pulses from a control unit such as control unit 120 described with respect to FIG. 1. The electrical pulses are utilized for cutaneous stimulation of a region of the body by transmission of the electrical pulses to a conductive skin contact area 239 via conductor 235. In one embodiment, conductor 235 is integral to conductive skin contact area 239, which is located on the inside of cylindrical electrode 200.

In one embodiment, conductive skin contact area 239 comprises conductive electrolytes for electrically coupling cylindrical electrode 200 to the skin in the form of fluids, gels, a flexible conductive fabric or material or the like. In one embodiment, conductive skin contact area 239 comprises a conductive adhesive gel for electrically coupling cylindrical electrode 200 to the skin. This conductive gel is adhesive in nature so that it may perform a dual function by both electrically coupling the electrode to the body and adhering the electrode to the body. In one embodiment, the conductive adhesive gel is disposed as a separate adhesive electrically conductive pad that is coupleable to stimulation electrode 200. Thus, only an expendable gel pad material need be disposable. In another embodiment, cylindrical stimulation electrode 200 is disposable.

Stimulation electrode 200 further includes a non-conductive skin contact area 237 located on the inside of cylindrical electrode 200. In one embodiment, stimulation electrode 200 includes an electrically insulative material 231 on the exterior of the cylindrical stimulation electrode. In one embodiment, the electrically insulative material 231 has elastic properties such that the cylindrical stimulation electrode 200 can be adjusted to fit many different sized fingers, ankles, wrists or the like. In another embodiment, stimulation electrode 200 includes a seam 269 that has elastic properties that allows the cylindrical stimulation electrode 200 to be adjusted to fit many different sized fingers, ankles, wrists or the like. In another embodiment, cylindrical electrode 200 adjusts to fit a variety of different sized body parts for example one size that fits a variety of upper arms, forearms, wrists, torsos, ankles, knees, calves, thighs or the like.

Figure 3:
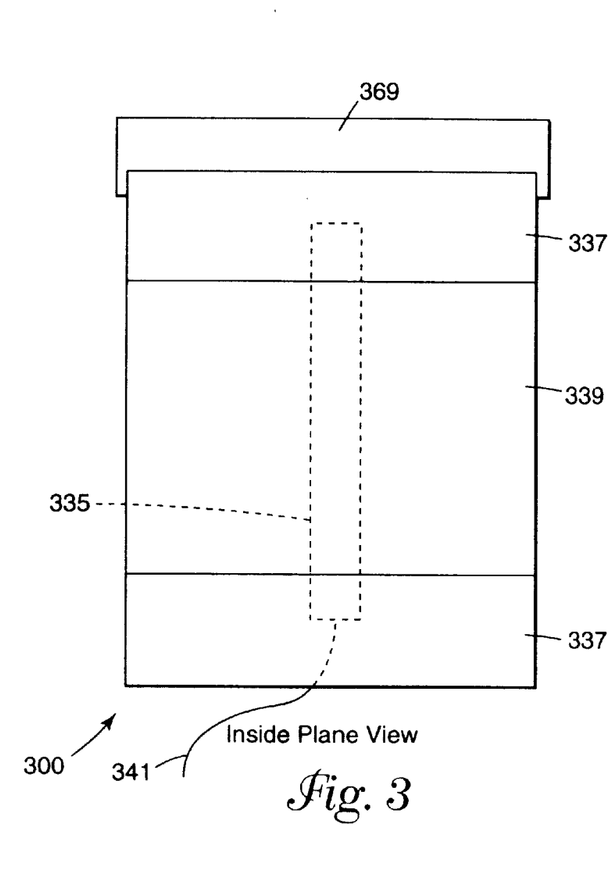
FIG. 3 is an illustration of an inside plane view of one embodiment of a cylindrical stimulation electrode constructed according to the teachings of the present invention.

FIG. 3 is an illustration of an inside plane view of one embodiment of a cylindrical stimulation electrode, shown generally at 300, constructed according to the teachings of the present invention. Stimulation electrode 300 includes a conductor 335 coupled to an electrical lead 341. Electrical lead 341 is coupled to and receives electrical pulses form a control unit such as control unit 120 described with respect to FIG. 1. The electrical pulses are utilized for cutaneous stimulation of a region of the body by transmission of the electrical pulses to a conductive skin contact area 339 via conductor 335. In one embodiment, conductor 335 is integral to conductive skin contact area 339.

In one embodiment, conductive skin contact area 339 comprises conductive electrolytes for electrically coupling stimulation electrode 300 to the skin in the form of fluids, gels, a flexible conductive fabric or material or the like. In one embodiment, conductive skin contact area 339 comprises a conductive adhesive gel for electrically coupling stimulation electrode 300 to the skin. In one embodiment, the conductive adhesive gel is disposed as a separate adhesive electrically conductive pad that is coupleable to stimulation electrode 300. The adhesive pad is disposable and replaced after each use. In another embodiment, stimulation electrode is disposed when wear dictates replacement.

Stimulation electrode 300 further includes a non-conductive skin contact area 337 coupled to either side of conductive area 339. In one embodiment, stimulation electrode 300 includes a seam 369 made of a material that has elastic properties such that the stimulation electrode 300 can be adjusted to fit different sizes of similar body parts. In one embodiment, cylindrical stimulation electrode 300 adjusts to fit a variety of different sized fingers. In another embodiment, cylindrical electrode 300 adjusts to fit a variety of different sized body parts for example one size that fits a variety of upper arms, forearms, wrists, torsos, ankles, knees, calves, thighs or the like.

Figure 4:
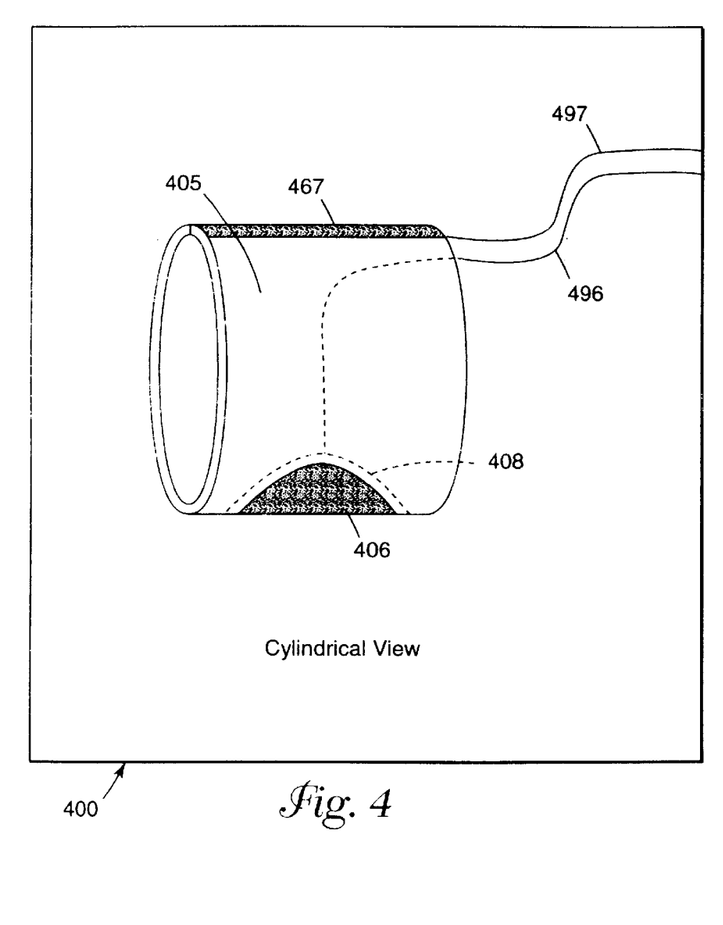
FIG. 4 is an illustration of a cylindrical view of one embodiment of a cylindrical tactile sensor constructed according to the teachings of the present invention.

FIG. 4 is an illustration of a cylindrical view of one embodiment of a cylindrical tactile sensor, shown generally at 400, constructed according to the teachings of the present invention. Tactile sensor 400 includes a pressure sensor 408 that is integral to the body 405 of the tactile sensor 400. The pressure sensor 408 is coupled to a first electrical lead 496 and a second electrical lead 497. The first and second electrical leads 496 and 497 are coupled to a control unit such as control unit 120 discussed with respect to FIG. 1. In one embodiment, the first lead 496 receives a request for information from the control unit and the second lead 497 provides a response signal to the control unit containing pressure information. In another embodiment, the first lead 496 and second lead 497 each provide pressure information to the control unit for a determination as to whether stimulation should be provided. In one embodiment, the body 405 of tactile sensor 400 is fabricated of a material that has elastic properties such that the tactile sensor 400 can be adjusted to fit many different sized fingers, ankles, wrists or the like. In another embodiment, the body 405 of tactile sensor 400 includes a seam 467 that is fabricated of a material that has elastic properties such that the tactile sensor 400 can be adjusted to fit many different sized body parts. In one embodiment, cylindrical tactile sensor 400 adjusts to fit a variety of different sized fingers. In another embodiment, cylindrical tactile sensor 400 adjusts to fit a variety of different sized body parts for example one size that fits a variety of upper arms, forearms, wrists, torsos, ankles, knees, calves, thighs or the like. In one embodiment, tactile sensor 400 includes a pad 406 coupled to pressure sensor 408. Pad 406 is made of a material, such as rubber, neoprene or the like, which aids in gripping. In an embodiment, where pressure sensor 400 fits on a finger tip, the pad 406 is adapted to aid in contacting buttons, switches, and the like.

Figure 5:
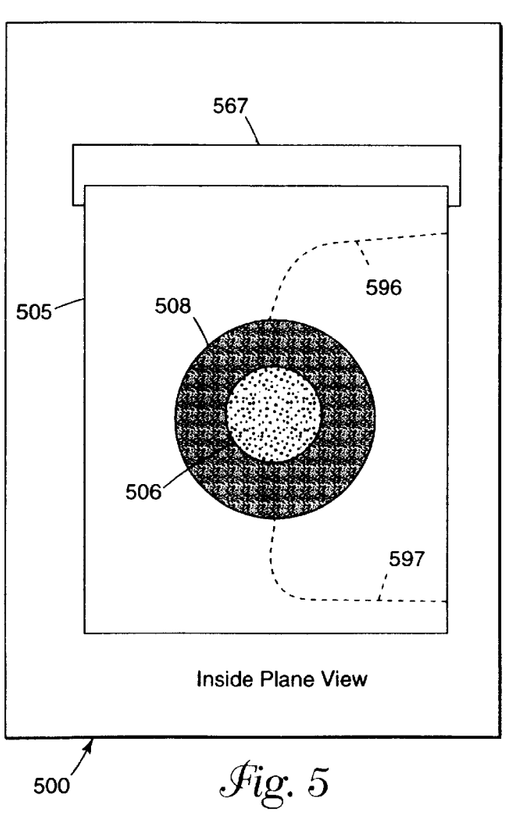
FIG. 5 is an illustration of an inside plane view of one embodiment of a cylindrical tactile sensor shown constructed according to the teachings of the present invention.

FIG. 5 is an illustration of an inside plane view of one embodiment of a cylindrical tactile sensor, shown generally at 500, constructed according to the teachings of the present invention. Tactile sensor 500 includes a pressure sensor 508 that is integral to the body 505 of tactile sensor 500. Pressure sensor 508 is coupled to a first and a second electrical lead 596 and 597 respectively. The first and second electrical leads 596 and 597 are coupled to a control unit such as control unit 120 discussed with respect to FIG. 1. In one embodiment, the first lead 596 receives a request for information from the control unit and the second lead 597 provides a response signal to the control unit containing pressure information. In another embodiment, the first lead 596 and second lead 597 each provide pressure information to the control unit for a determination as to whether stimulation should be provided. In one embodiment, the body 505 of tactile sensor 500 is fabricated of a material that has elastic properties such that tactile sensor 500 can be adjusted to fit many different sized body parts. In another embodiment, the body 505 of tactile sensor 500 includes a seam 567 that is fabricated of a material that has elastic properties. In one embodiment, cylindrical tactile sensor 500 adjusts to fit a variety of different sized fingers. In another embodiment, cylindrical tactile sensor 500 adjusts to fit a variety of different sized body parts for example one size that fits a variety of upper arms, forearms, wrists, torsos, ankles, knees, calves, thighs or the like. In one embodiment, tactile sensor 500 includes a pad 506 coupled to pressure sensor 508. Pad 506 is made of a material, such as rubber, neoprene or the like, which aids in gripping. In an embodiment, where pressure sensor 500 fits on a finger tip, the pad 506 will aid in contact with buttons, switches, and the like.

Figure 6:
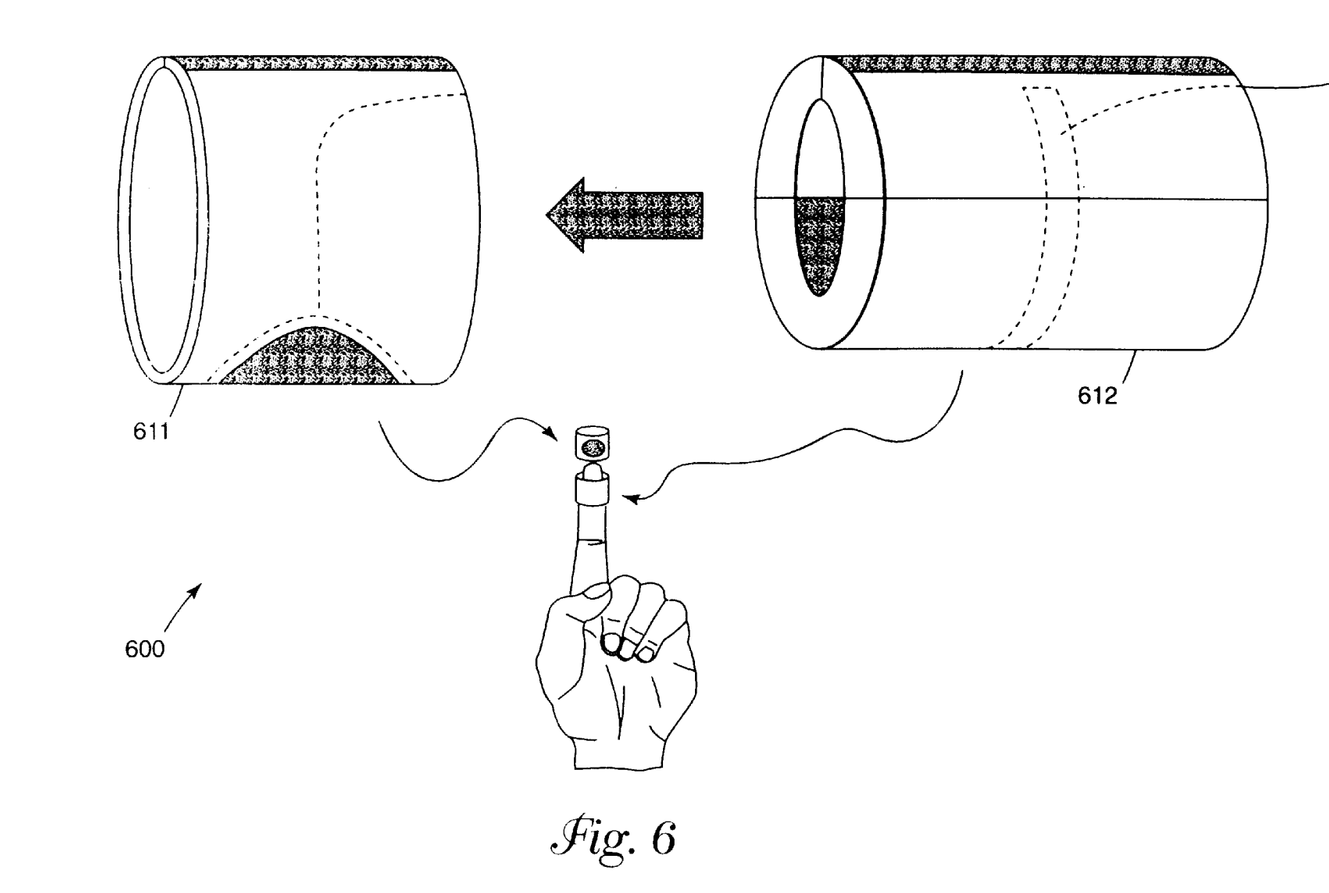
FIG. 6 is an illustration of one embodiment of an assembly for a cylindrical tactile sensor and a cylindrical stimulation electrode insert cylindrical tactile sensor constructed according to the teachings of the present invention.

In one embodiment, a cylindrical tactile sensor such as 400 or 500 fits together with a stimulation electrode such as 200 or 300 to create an assembly used to monitor pressure at a location on the body and provide electrical stimulation to that area. In one embodiment, tactile sensor 400 or 500 fits over stimulation electrode 200 or 300 to form a single integrated assembly. FIG. 6 is an illustration of one embodiment of an assembly 600 for a cylindrical tactile sensor 611 and a cylindrical stimulation electrode insert 612. In one embodiment, this assembly is coupled to a control unit such as 120 discussed with respect to FIG. 1. The control unit monitors the pressure measurements received and adaptively stimulates the area of the body that the adhesive conductor of the stimulation electrode comes in contact with in order to provide a cue to produce an appropriate response. For example in one embodiment, the assembly is used to monitor pressure measurements at a fingertip. When the monitored pressure measured by the tactile sensor meets a defined threshold for that assembly location, the control unit generates stimulation waveforms having a defined pulse width, amplitude, frequency, and waveform shape for stimulation of the area based on the specific application. In this manner, finger movement timing for patients suffering from Parkinson's disease can be improved or restored. Cutaneous stimulation is applied or modified when a finger is pressed against a surface provides an orienting tactile cue. In one embodiment, this cue provides a cadence, enabling timed repetitive action.

Figure 7:
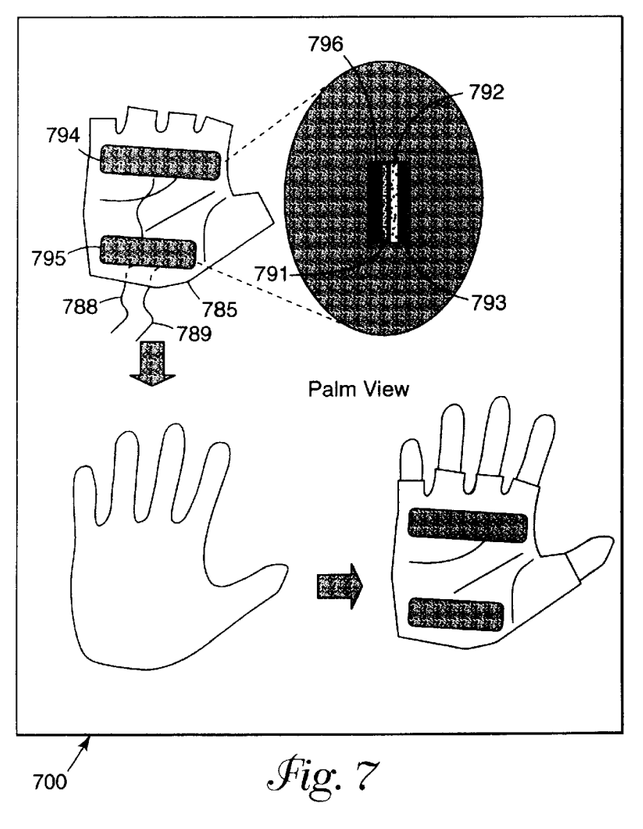
FIG. 7 is an illustration of a palm view of one embodiment of a tactile sensor and stimulation glove constructed according to the teachings of the present invention.

FIG. 7 is an illustration of a palm view of one embodiment of a tactile sensor and stimulation glove, shown generally at 700, constructed according to the teachings of the present invention. A glove 785 includes a first and a second tactile sensor assembly 794 and 795 respectively. In one embodiment, each tactile sensor assembly includes a stimulation electrode 793, which is in direct contact with the palm of the hand, glove material 792 sandwiched between the electrode 793 and a pressure sensor 791, and a gripping material 796, such as rubber, neoprene, or the like, on top of pressure sensor 791. The first tactile sensor assembly 794 is coupled to a first electrical lead 788 and the second tactile sensor assembly 795 is coupled to a second electrical lead 789. Each electrical lead 788 and 789 is coupled to a control unit such as control unit 120 discussed with respect to 120. In one embodiment, the electrical leads provide pressure information to a control unit for a determination of the need for stimulation. In one embodiment, glove 785 is fabricated of a material having elastic properties to aid in fitting a variety of different sized hands.

Figure 8:
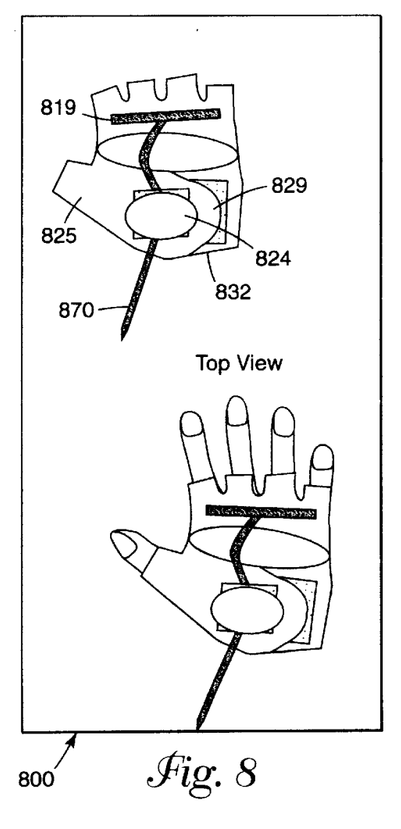
FIG. 8 is an illustration of a top view of one embodiment of a tactile sensor and stimulation glove constructed according to the teachings of the present invention.

FIG. 8 is an illustration of a top view of one embodiment of a tactile sensor and stimulation glove, shown generally at 800, constructed according to the teachings of the present invention. The glove 825 includes a wire connector 819 for connection to additional sensors such as pressure sensor assemblies attached to one or more fingers or thumb, acceleration or pressure sensors attached to the wrist, forearm, upper arm or the like. Wire connector 819 includes a connection cable 870 for coupling to a control unit, such as control unit 120, of FIG. 1. In one embodiment, connection cable 870 comprises all of the wiring to and from the control unit for stimulation and transmission of sensor information. In addition, stimulation glove 825 includes a common return electrode 832. Common return electrode 832 is in direct contact with the skin and provides the return path for each of the electrical stimulation electrodes attached to the body. It provides a large surface and as a result a lower impedance than each of the stimulation electrodes, this is adapted to aid in keeping the current at the contact location at a comfortable level for the patient. In one embodiment, the common return path includes a lead coupled to the control unit. In another embodiment, the common return path includes a lead within connection cable 870 coupled to the control unit.

In one embodiment, glove 825 includes a strain relief 827 in order to adjust the placement of connection cable 870. In one embodiment, glove 825 includes an adjustable flap 829 which is secured with attachment devices such as snaps, buckles, straps, hook and pile or the like. In one embodiment, glove 825 is fabricated of a material having elastic properties. In one embodiment, the features of stimulation glove 785 of FIG. 7 and the features of stimulation glove 825 are combined to create an integrated tactile sensor and stimulation glove which is coupled to a control unit such as control unit 120 of FIG. 1. In one embodiment, the integrated tactile sensor and stimulation glove 825 includes one or more of the following features: one or more fingertip/thumb pressure/stimulation assemblies, one or more pressure/stimulation assemblies mounted on the palm of the glove, fabricated of flexible material, a wire connector such as 819, a connection cable such as 870, an adjustable flap such as 829 and a strain relief such as 827.

Figure 9:
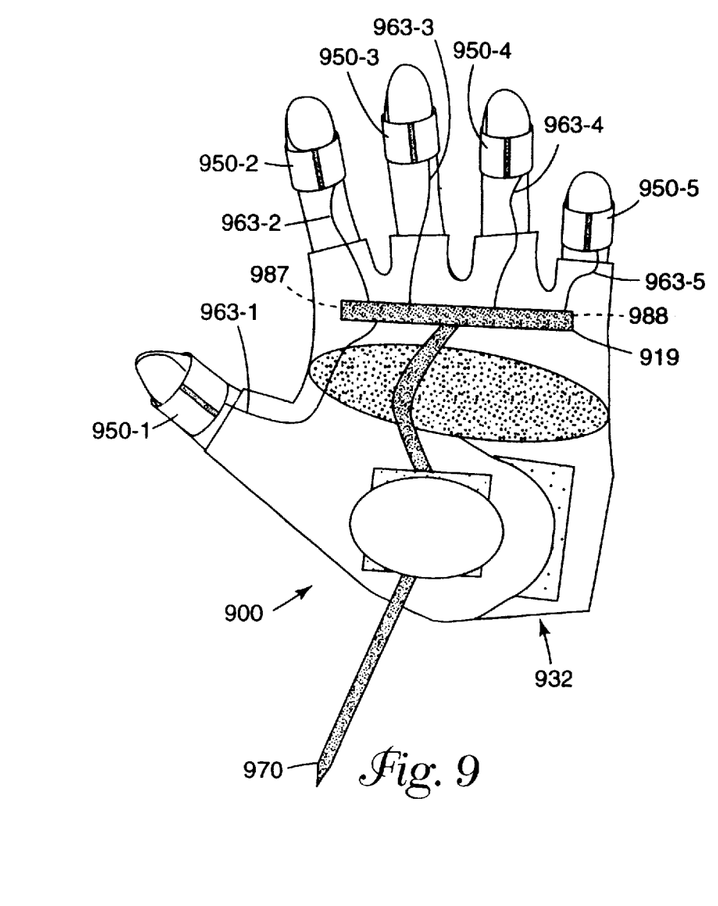
FIG. 9 is an illustration of a top view of one embodiment of a tactile sensor and stimulation glove integrated with finger sensors constructed according to the teachings of the present invention.

FIG. 9 is an illustration of a top view of one embodiment of a tactile sensor and stimulation glove integrated with finger sensors, shown generally at 900, constructed according to the teachings of the present invention. Glove 900 includes a wire connector 919 coupled to electrical leads 963-1 to 963-5 that are coupled to tactile sensor and stimulation electrode assemblies 950-1 to 950-5 respectively. In one embodiment, wire connector 919 is coupled to electrical leads 987 and 988 that are coupled to first and second tactile sensors (not shown), such as sensors 794 and 795 of FIG. 7. Glove 900 further includes a connection cable 970 that connects wire connector 919 to a control unit, such as control unit 120 of FIG. 1. In addition, glove 900 includes a common return electrode 932. In one embodiment, glove 900 includes one or more tactile sensor and stimulation electrode assemblies 950 as required for each application. In an alternate embodiment, additional electrode stimulators may also be attached to stimulate forearm, upper arm, and shoulder.

Figure 10:
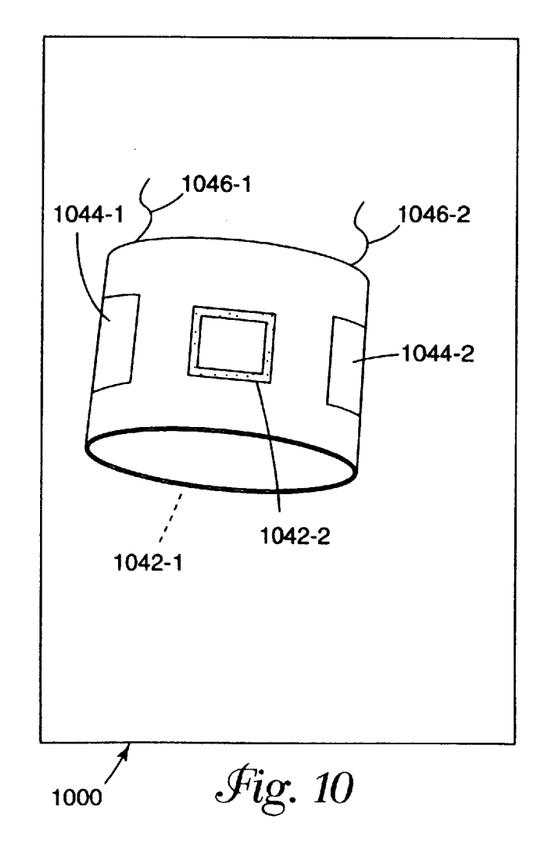
FIG. 10 is an illustration of one embodiment of a stimulation and sensing wristband constructed according to the teachings of the present invention.

FIG. 10 is an illustration of one embodiment of a stimulation and sensing wristband, shown generally at 1000, constructed according to the teachings of the present invention. Wristband 1000 includes first and second stimulation electrodes 1044-1 and 1044-2 located on the left and right sides of the wrist. In one embodiment, wristband 1000 includes a first and a second acceleration sensor (accelerometers) 1042-1 and 1042-2 located on the top and bottom sides of the wrist. Wristband 1000 includes a first and a second electrical lead 1046-1 and 1046-2 coupled to the first and second stimulation electrodes 1044-1 and 1044-2, respectively. In one embodiment, the electrical leads 1046-1 and 1046-2 couple to a common wire connector such as the wire connector 919 of FIG. 9. In another embodiment, the electrical leads 1046-1 and 1046-2 are directly coupled to a control unit such as control unit 120 discussed with respect to FIG. 1. Electrical stimulation signals and electrical information signals are sent and received via the electrical leads 1046-1 and 1046-2. In one embodiment, wristband 1000 is fabricated of a material that has elastic properties such that the wristband is adjustable to fit a variety of different sized wrists. It is understood that the number and placement of stimulation electrodes and sensors are for illustration and alternate embodiments may include an appropriate configuration of stimulation electrodes and types of sensors for each application.

Figures 11, 13:
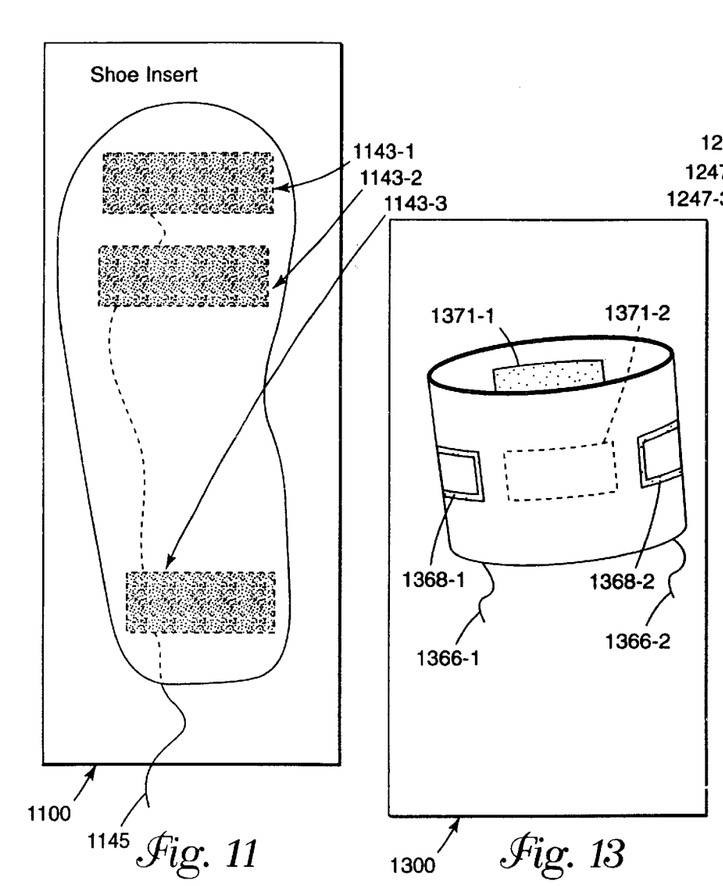
FIG. 11 is an illustration of one embodiment of a shoe insert constructed according to the teachings of the present invention.
FIG. 13 is an illustration of one embodiment of a stimulation and sensing ankle band constructed according to the teachings of the present invention.

FIG. 11 is an illustration of one embodiment of a shoe insert, shown generally at 1100, constructed according to the teachings of the present invention. In one embodiment, shoe insert 1100 includes first, second and third pressure sensors 1143-1 to 1143-3 located under the toes, on the ball of the foot and on the heel of the foot respectively. In addition, shoe insert 1100 includes an electrical lead 1145 coupled to each of pressure sensors 1143-1 to 1143-3. In one embodiment, electrical lead 1145 is coupled to a control unit such as control unit 120 discussed with respect to FIG. 1. Pressure information is transmitted to the control unit for a determination of the need for stimulation. In an alternate embodiment, shoe insert 1100 includes any number of electrical leads attached to sensors based on each application. It is understood that the number, type and location of sensors 1143 are for illustration only and alternate embodiments may include an appropriate configuration of sensors for each application.

Figure 12:
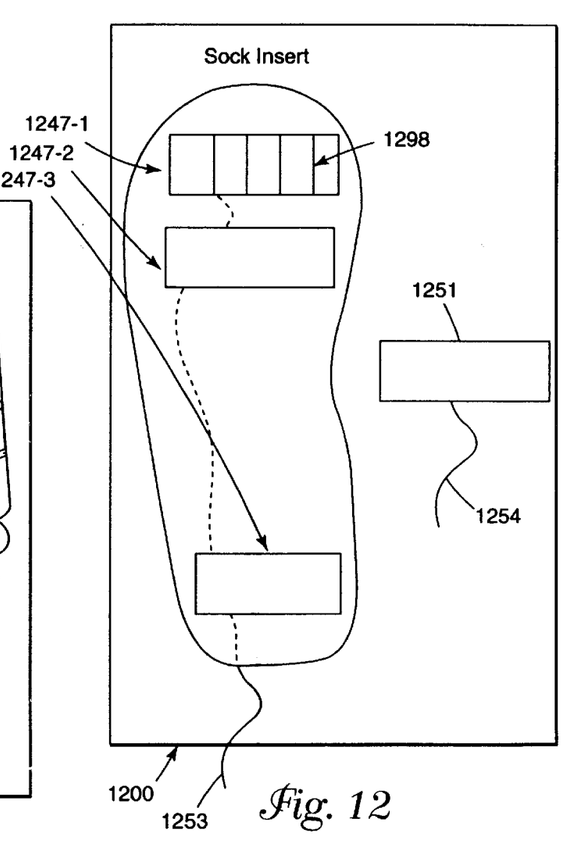
FIG. 12 is an illustration of one embodiment of a sock insert constructed according to the teachings of the present invention.

FIG. 12 is an illustration of one embodiment of a sock insert, shown generally at 1200, constructed according to the teachings of the present invention. In one embodiment, sock insert 1200 includes stimulation electrodes 1247-1 to 1247-3. In one embodiment, stimulation electrodes 1247-1 to 1247-3 include an adhesive conductive gel pad that is in direct contact with the foot. In one embodiment, stimulation electrode 1247-1 is located under the toes and includes ridges 1298 to aid in cupping the toes for direct contact with the toes. Sock insert 1200 includes electrical lead 1253 that is coupled to each of stimulation electrodes 1247-1 to 1247-3. In one embodiment, electrical lead 1253 is in coupled to a control unit such as control unit 120 of FIG. 1. Electrical pulses are transmitted to each of stimulation electrodes 1247-1 to 1247-3 as required for each application. In an alternate embodiment, sock insert 1200 includes any number of electrical leads attached to stimulation electrodes in order to control stimulation to the foot based on each application. Sock insert 1200 includes a common return electrode 1251 that is attached to the top of the foot. Common return electrode 1251 is coupled to electrical lead 1254 that is coupled to the control unit and provides the return path for the electrical stimulation pulses.

In one embodiment, shoe insert 1100 and sock insert 1200 are integrated to create an adaptive electrical stimulator.

FIG. 13 is an illustration of one embodiment of a stimulation and sensing ankle band, shown generally at 1300, constructed according to the teachings of the present invention. Ankle band 1300 includes first and second stimulation electrodes 1371-1 and 1371-2 located on the front and back sides of the ankle, respectively. In one embodiment, ankle band 1300 includes first and second acceleration sensors (accelerometers) 1368-1 and 1368-2 located on the left and right sides of the ankle, respectively. Ankle band 1300 includes first and second electrical leads 1366-1 and 1366-2 coupled to the first and second stimulation electrodes 1371-1 and 1371-2 respectively. In one embodiment, electrical leads 1366-1 and 1366-2 are coupled to a control unit such as control unit 120 of FIG. 1. Electrical stimulation pulses are provided to stimulation electrodes 1371 and 1371-2 via electrical leads 1366-1 and 1366-2, respectively. Ankle band 1300 includes electrical leads (not shown) from the control unit to acceleration sensors 1368-1 and 1368-2 in order to receive acceleration information. In one embodiment, ankle band 1300 is fabricated of a material that has elastic properties such that the ankle band is adjustable for a variety of different sized ankles. It is understood that the number and placement of stimulation electrodes and sensors are for illustration and alternate embodiments may include an appropriate configuration of stimulation electrodes and types of sensors for each application.

Figure 14:
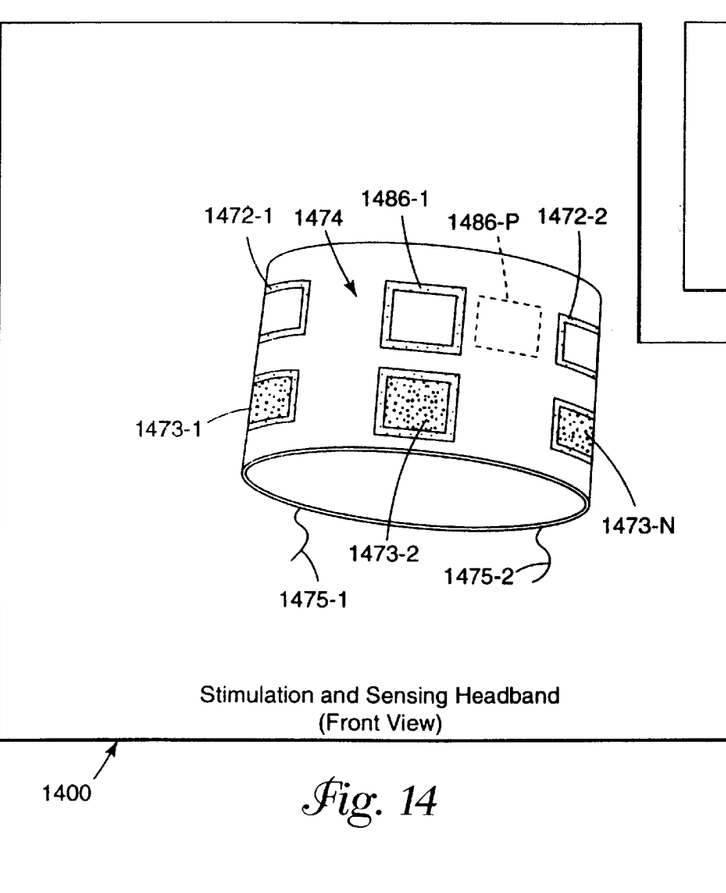
FIG. 14 is an illustration of one embodiment of a stimulation and sensing headband constructed according to the teachings of the present invention.

FIG. 14 is an illustration of one embodiment of a stimulation and sensing headband, shown generally at 1400, constructed according to the teachings of the present invention. Headband 1400 includes a first and a second stimulation electrode 1472-1 and 1472-2 located on the right and left front of the head, respectively. In addition, headband 1400 includes a first electrical lead 1475-1 coupled to the first stimulation electrode 1472-1 and a second electrical lead 1475-2 coupled to the second stimulation electrode 1472-2. The first and second electrical leads 1475-1 and 1475-2 are each coupled to a control unit such as control unit 120 of FIG. 1. The control unit transmits electrical stimulation signals to the electrical stimulation electrodes 1472-1 and 1472-2 via electrical leads 1475-1 and 1475-2 respectively. Electrical stimulation electrodes 1472-1 and 1472-2 are in direct contact with the skin. In one embodiment, electrical stimulation electrodes 1472-1 and 1472-2 each comprise conductive adhesive gel for electrically coupling the electrodes to the skin. In one embodiment, headband 1400 includes accelerometers 1486-1 to 1486-P as required for each application. In one embodiment, accelerometers 1486-1 to 1486-P are located on the sides, front and back of the head. In one embodiment, headband 1400 includes inclination sensors 1473-1 to 1473-N as required for each application. In one embodiment, inclination sensors 1473-1 to 1473-N are located on the sides, front and back of the head. It is understood that the number and placement of stimulation electrodes and sensors are for illustration and alternate embodiments may include an appropriate configuration of stimulation electrodes and types of sensors for each application.

Figure 15:
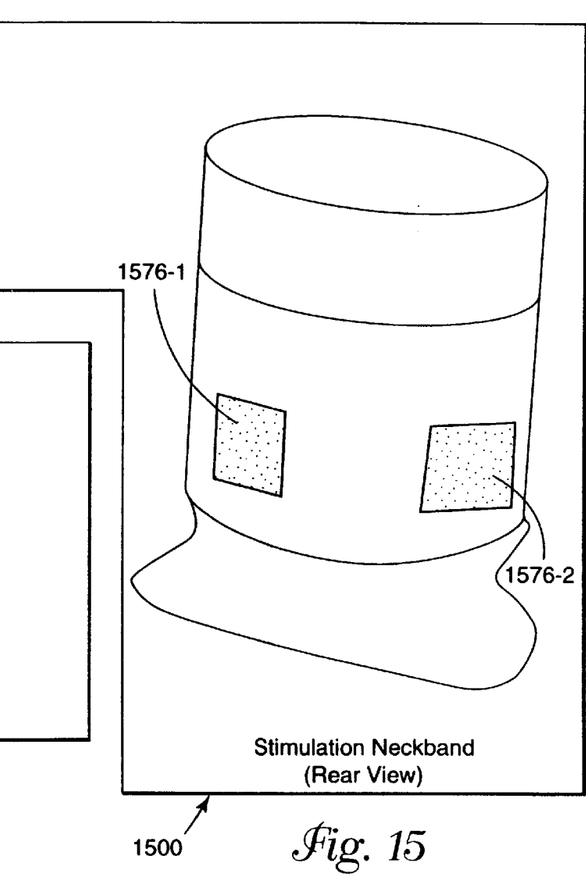
FIG. 15 is an illustration of one embodiment of a stimulation neckband constructed according to the teachings of the present invention.

FIG. 15 is an illustration of one embodiment of a stimulation neckband, shown generally at 1500, constructed according to the teachings of the present invention. Stimulation neckband includes stimulation electrodes 1576-1 and 1576-2. In one embodiment, stimulation electrodes 1576-1 and 1576-2 are located at the left and right rear of the neck. In alternate embodiments, stimulation electrodes such as 1576 are strategically located for the specific application. In one embodiment, each stimulation electrode 1576-1 and 1576-2 is coupled to an electrical lead (not shown) that is coupled to a control unit such as control unit 120 and transmits electrical stimulation pulses from the control unit to the electrode. In one embodiment, stimulation neckband includes inclination sensors coupled to the control unit. The inclination sensors provide inclination information for a determination by the control unit for the need for stimulation. It is understood that the number and placement of stimulation electrodes and sensors are for illustration and alternate embodiments may include an appropriate configuration of stimulation electrodes and types of sensors for each application.

In one embodiment, impaired voluntary movements (akinesia) are broken using aural, visual, or tactile external stimulation. Synthesized tactile stimulation with an adaptive stimulator will provide the cues to enable properly timed repetitive motion.

Figure 16:
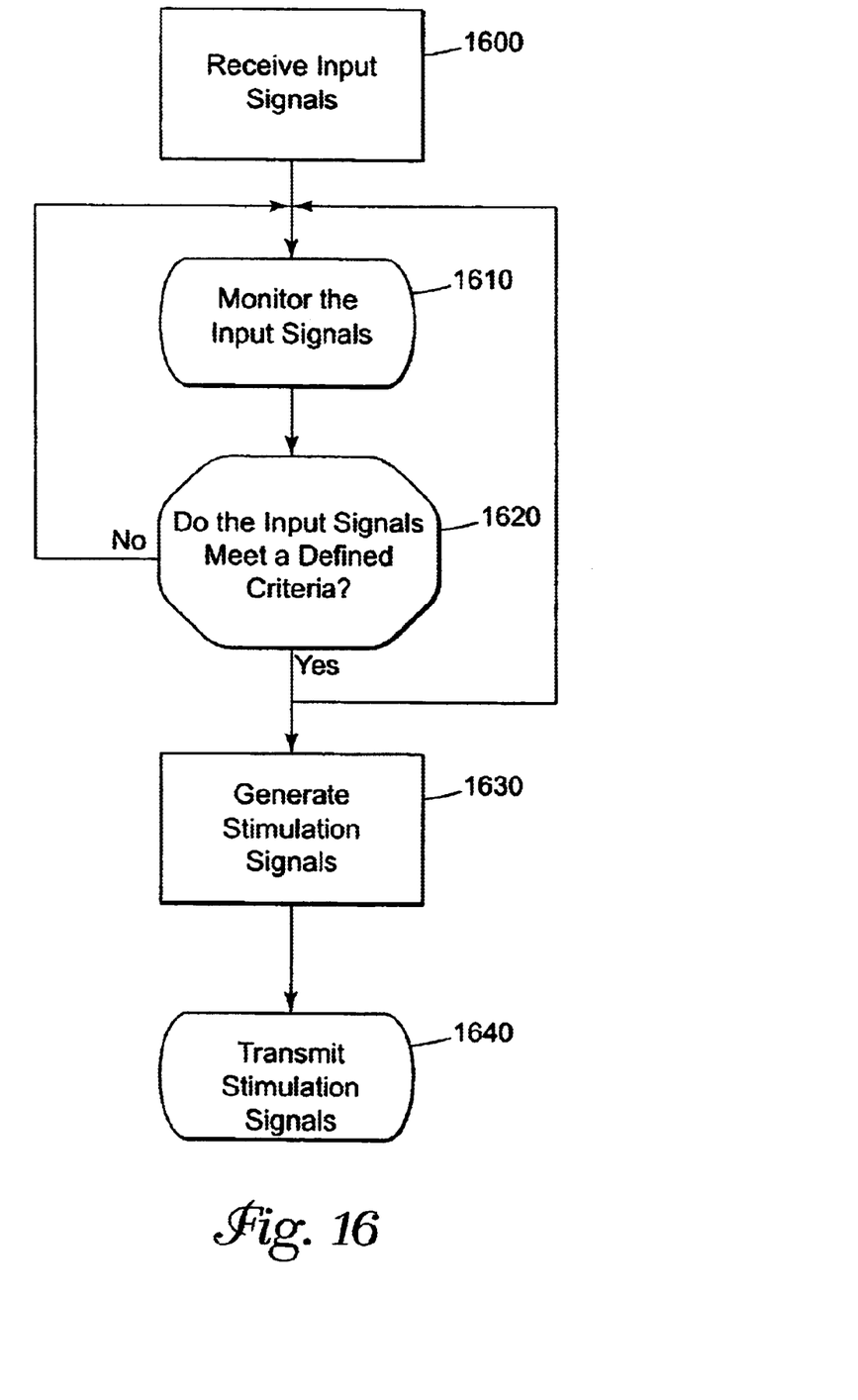
FIG. 16 is a flow diagram of one embodiment of method of adaptive stimulation for the treatment of the symptoms of Parkinson's disease according to the teachings of the present invention.

FIG. 16 is a flow diagram of one embodiment of a method of adaptive stimulation for the treatment of the symptoms of Parkinson's disease according to the teachings of the present invention. The method at 1600 receives one or more input signals from at least one sensor such as pressure, inclination, acceleration or the like, wherein the input signals are based on physical stimulus. The method proceeds to 1610 and monitors the received input signals. The method then proceeds to 1620 and determines if the input signals meet defined criteria. If the input signals meet defined criteria the method proceeds to 1630 and generates one or more stimulation signals. If the input signals do not meet defined criteria, the method proceeds to 1610 and continues to monitor the input signals. In addition, when the input signals meet defined criteria the method continues to monitor the input signals while the method proceeds. Once the stimulation signals are generated the method proceeds to 1640 and transmits the one or more stimulation signals to one or more stimulators.

In one embodiment, the method further includes monitoring stimulation electrode voltage and current to prevent exposure of the patient to uncomfortable stimulation levels.

In one embodiment, the input signals include pressure, acceleration, inclination information and the like from strategically positioned sensors. In alternate embodiments, the input signals include information from an operator control panel and/or a remotely located processing unit. In one embodiment, an operator to include the patient, a technician, a physician or the like controls the input signals from the operator control panel.

In one embodiment, the input signals are received from a number of sensors for example pressure and acceleration sensors that are mounted on one or more wearable devices such as a headband, a wristband and/or an ankle band. In an alternate embodiment, input signals include operator control signals. A control unit receives the input signals and determines a response based on the input signals. In one embodiment, the response may include aural stimulation, electrical stimulation, and/or sonic stimulation as well as frequency, amplitude, pulse width, waveform shape and duration of stimulation. In one embodiment, the response to input signals includes cadence simulation, tactile simulation, sequenced stimulation or the like.

In one embodiment, the control unit transmits information about the inputs or the stimulation signals to a display. In another embodiment, the control unit wirelessly transmits information to a remote processing unit for data collection or processing.

For example, in one embodiment, the control unit receives inputs that indicate little or no motion (acceleration) at the wrist, potentially signaling that the patient has stopped swinging his/her arm while walking, the patient has stopped walking, the patient is having trouble initiating movement in the arm and the like. As a response the control unit provides stimulation at the wrist in a cadence that emulates the patients normal gait or a stimulation at one or more of the wrist, forearm, hand, upper arm or the like, to cue the patient to move their arm. Each application of an adaptive stimulator is individualized and requires criteria for each patient. The control unit is programmable for each patient to respond based on a set of criteria. In one embodiment, a control unit is programmed to provide electrical stimulation and if the electrical stimulation does not produce the desired result the control unit will adapt to change the voltage, frequency, pulse width, amplitude, waveform and/or the like of the electrical stimulation signals. In an alternate embodiment, the control unit detects that the provided stimulation has not produced the desired result and changes the type of stimulation e.g. from electrical to aural, from aural to electrical, or the like. In a further embodiment, the control unit changes the sequence or the cadence of the stimulation.

In one embodiment, the stimulators comprise stimulation electrodes. In an alternate embodiment, the stimulators comprise sonic stimulators. In a further embodiment, the stimulators comprise aural stimulators. It is understood that the number and type of stimulators is not limited and adaptively stimulating a region of the body to aid in treatment of the symptoms of Parkinson's disease may include any number or type of stimulators and stimulator combinations. In addition, each application can be individualized.

Figure 17:
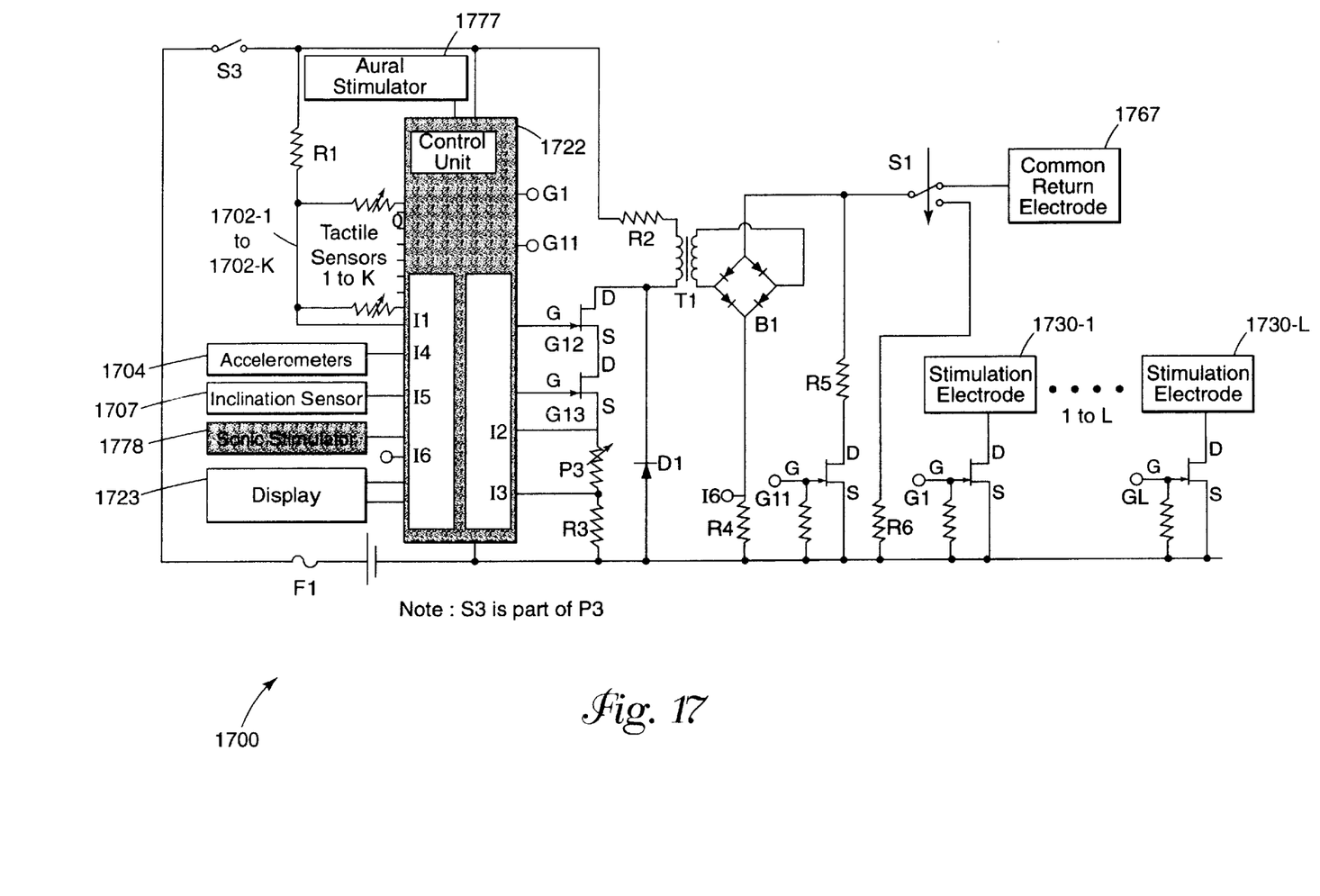
FIG. 17 is a schematic of one embodiment of an adaptive stimulator according to the teachings of the present invention.

FIG. 17 is a schematic of one embodiment of an adaptive stimulator, shown generally at 1700, constructed according to the teachings of the present invention. Stimulator 1700 includes a control unit 1722 and a plurality of sensors coupled to the control unit. The sensors include but are not limited to accelerometers 1704, inclination sensors 1707, and tactile sensors 1702-1 to 1702-K. In one embodiment, the tactile sensors 1702-1 to 1702-K include pressure sensors. In one embodiment, control unit 1722 is also coupled to a plurality of stimulators to include an aural stimulator 1777, stimulation electrodes 1730-1 to 1730-L and sonic stimulator 1778. In addition, stimulator 1700 includes a display and control panel 1723. In one embodiment, the display is a liquid crystal display.

In operation, the control unit 1722 receives information from one or more sensors 1704, 1707, 1702 and determines when and if aural, electrical, sonic or the like stimulation is required. The control unit 1722 then provides the required stimulation and continues to monitor information received and adapts to modify the type of stimulation, duration, frequency, amplitude and the like in order to produce the desired results, e.g., movement of a finger or fingers, legs, arm or the like, lifting of the head, movement of the body, etc. In one embodiment, control unit 1722 collects and stores information about inputs to and outputs from control unit 1722. In one embodiment, the information is stored in a database or memory device.

In one embodiment, timing signals are generated by micro-code of control unit 1722. The micro-code determines the pulse width and frequency for each pulse. For each pulse generated, power field effect transistors (FETs) G12 and G13 are gated "on" to allow current flow through the primary of the transformer T1. In this embodiment, two field effect transistors G12 and G13 are used and individually controlled to prevent a single input/output or FET failure from applying a continuous direct current to the transformer T1.

Current flows through the current limiting resistor R2, the transformer T1 primary, FETs G12 and G13, amplitude control potentiometer P3, and current monitoring resistor R3 inducing a current in the secondary. FET G12 is then gated off and current flows through diode D1. Amplitude control is provided by potentiometer P3 through primary field current limiting. Monitoring of analog inputs 12 and 13 provides an indication of the voltage applied to and current flowing through the primary. Using the turn's ratio, secondary voltage and current may be approximated.

Secondary voltage is rectified using a full wave bridge B1. The positive side of the bridge is connected to the positive return electrode. A single stimulation electrode 1730-1 to 1 730-L is enabled for each pulse out of the transformer secondary. Current monitoring resistor R4 provides the mechanism for monitoring of secondary current by the control unit 1733 through analog input 16. Enabling FET G11 facilitates monitoring of a fixed load secondary voltage. This enables current flow through resistor R5 forming a resistive bridge with current monitoring resistor R4. Based on current flow and known resistance value R5, secondary voltage may be approximated.

In one embodiment, a manual shunt of the stimulation electrode voltage is accomplished through human activation of switch S1. This disconnects the common return electrode 1767 and shunts the current through resistor R6. This produces a transformer secondary over-current status condition in control unit 1722 that shuts down the pulse generation on the primary. In one embodiment, the control unit 1722 will then attempt to reset the pulse generation every three to five seconds while continuing to disable the stimulation electrodes 1730-1 to 1730-L. The stimulation electrodes 1730-1 to 1730-L will not be enabled until it is determined that the voltage adjustment potentiometer P3 has been readjusted to a lower value.

CONCLUSION

An adaptive stimulator has been described. The stimulator includes a control unit and at least one stimulation electrode coupled to an output of the control unit. The at least one stimulation electrode is adapted to provide stimulation to an area of the body of a living subject. The adaptive stimulator includes at least one sensor coupled to the control unit and adapted to be disposed external to the human body. The sensor is adapted to respond to physical stimulus and provide input to the control unit. The adaptive stimulator is adapted to selectively provide stimulation in response to the control unit.

In addition, a method of adaptive stimulation has been described. The method includes receiving one or more input signals. At least one of the input signals is based on physical stimulus. The method also includes monitoring the received input signals and selectively generating one or more stimulation signals when the one or more input signals meet defined criteria. The method further includes transmitting the one or more stimulation signals to an area of the body of a living subject. The one or more stimulation signals aid in the relief of symptoms of neurological disorders.

Further, a control unit adapted to aid in the relief of symptoms of Parkinson's disease has been described. The control unit includes an input that is adapted to couple to one or more sensors that are adapted to respond to physical stimulus. The control unit also includes a controller that is coupled to the input and a waveform generator coupled to the controller. The control unit further includes an output coupled to the controller and adapted to couple to one or more stimulation electrodes that are adapted to provide stimulation to an area on the human body. In addition, the control unit includes a stimulation voltage pulse generator coupled to the controller.

Although specific embodiments have been illustrated and described herein, it will be appreciated by those of ordinary skill in the art that any arrangement, which is calculated to achieve the same purpose, may be substituted for the specific embodiments shown. For example, although this technology is primarily being developed to relieve symptoms of neurological diseases, it has potential for application in other areas. These include symptomatic relief for other disorders, such as, Huntington's disease and rehabilitation therapy for neurological damage. Other applications may include incorporation into flight suits to prevent spatial disorientation of aircrew undergoing high acceleration maneuvers and potential for relieving symptoms of motion sickness. In addition, although the device is primarily designed for an electrical stimulation output stage, it can be modified to provide topical, sonic, aural stimulation or the like.

This application is intended to cover any adaptations or variations of the present invention. Therefore, it is intended that this invention be limited only by the claims and the equivalents thereof.

What it is claimed is:

1. A method of cueing an individual exhibiting one or more symptom's of Parkinson's disease, the method comprising:

monitoring one or more input signals from at least one sensor, wherein the input signals are based on physical stimulus;

generating one or more sensory cues when the one or more input signals meet a desired criteria indicating impaired voluntary movements;

wherein generating one or more sensory cues includes transmitting stimulation signals to one or more stimulators; and wherein the stimulators comprise aural stimulators, visual stimulators and tactile stimulators.

2. The method of claim 1, wherein the one or more symptoms of Parkinson's disease comprise tremor, rigidity, akinesia, bradykinesia and drooping head.

3. The method of claim 1, wherein monitoring one or more input signals from at least one sensor comprises monitoring one or more input signals from at least one sensor, wherein the at least one sensor comprises inclination sensors, acceleration sensors, and pressure sensors.

4. The method of claim 1, wherein the at least one sensor and one of the one or more stimulators form a single integrated device.

5. The method of claim 1, wherein generating one or more sensory cues comprises generating one or more sensory cues wherein the one or more sensory cues include tactile cues, aural cues, and visual cues.

6. The method of claim 1, further comprising modifying the one or more sensory cues when the input signals indicate the impaired voluntary movement is not broken.

7. The method of claim 6, wherein modifying the one or more sensory cues comprises modifying one or more of the voltage, frequency, pulse width, amplitude, and waveform of the stimulation signals.

8. The method of claim 6, wherein modifying the one or more sensory cues includes altering the cadence of the one or more sensory cues.

9. The method of claim 1, further comprising producing sequenced stimulation patterns.

10. The method of claim 1, wherein generating one or more sensory cues comprises synthesizing two or more of frequency, amplitude, pulse width, waveform shape and duration of stimulation.

11. An adaptive stimulator for cueing an individual exhibiting one or more symptom's of Parkinson's disease, comprising:

means for receiving input signals from one or more sensors, wherein the input signals are based on human body functions;

means for determining impaired voluntary movement based on the input signals;

means for generating one or more sensory cues, when impaired voluntary movement is determined;

wherein the one or more sensory cues include tactile cues, aural cues, and visual cues;

means for selectively transmitting stimulation signals to produce the one or more sensory cues;

means for controlling the means for selectively transmitting stimulation signals and the sensory cues; and means for selectively adjusting the one or more sensory cues when the impaired voluntary movement is not broken.

12. The stimulator of claim 11, further comprising:

means for monitoring stimulation signal voltage and current and modifying the stimulation signal voltage and current to prevent exposure of the individual to uncomfortable stimulation levels.

13. The stimulator of claim 11, wherein the means for generating one or more sensory cues comprises means for generating one or more sensory cues that simulate the cadence of unimpaired voluntary movements.

14. The stimulator of claim 11, wherein the impaired voluntary movement comprises one or more of tremor, rigidity, akinesia, bradykinesia and drooping head.

15. The stimulator of claim 11, wherein the human body functions include tactility, movement and placement.

16. The stimulator of claim 11, wherein the means for selectively adjusting the one or more sensory cues comprises means for altering the cadence of the one or more sensory cues.

17. The stimulator of claim 11, wherein the means for selectively adjusting the one or more sensory cues comprises means for adjusting the perceived intensity of the one or more sensory cues.

18. The stimulator of claim 11, further comprising means for storing information about the input signals and the stimulation signals.

19. The stimulator of claim 18, wherein the means for storing information comprises a means for storing information about the input signals including the number and type of sensory cues.

20. The stimulator of claim 11, wherein the means for generating tactile cues comprises means for generating tactile cues using one or more of cutaneous electrical stimulation and sonic stimulation.

21. The stimulator of claim 20, wherein the means for selectively adjusting the one or more sensory cues includes a means for adjusting voltage and current of the tactile cues.

22. The stimulator of claim 20, further comprising means for preventing exposure of the individual to uncomfortable stimulation levels by monitoring the voltage and current of the tactile cues and feeding the information back to a control unit for further processing.

23. The stimulator of claim 11, further comprising means for producing sequenced stimulation patterns.

* * * * *